(12) United States Patent
Wang (10) Patent No.: US 9,662,191 B2
(45) Date of Patent: May 30, 2017

(54) DENTAL LIGHT CURING DEVICE

(71) Applicant: MONITEX INDUSTRIAL CO., LTD., New Taipei (TW)

(72) Inventor: Shu-Lung Wang, New Taipei (TW)

(73) Assignee: MONITEX INDUSTRIAL CO., LTD., New Taipei (TW)

( * ) Notice: Subject to any disclaimer, the term of this patent is extended or adjusted under 35 U.S.C. 154(b) by 27 days.

(21) Appl. No.: 14/794,365

(22) Filed: Jul. 8, 2015

(65) Prior Publication Data

US 2017/0007385 A1    Jan. 12, 2017

(51) Int. Cl.
*A61C 19/00*    (2006.01)
*A61C 13/15*    (2006.01)
*A61C 1/00*     (2006.01)

(52) U.S. Cl.
CPC .......... *A61C 19/004* (2013.01); *A61C 1/0015* (2013.01)

(58) Field of Classification Search
CPC ..... A61C 19/00; A61C 19/003; A61C 1/0007; A61C 1/0015; A61C 1/0069; A61C 13/14
USPC .... 433/28, 29; 250/552, 553, 338.4, 339.03, 250/341.4, 370.01, 341.6
See application file for complete search history.

(56) References Cited

U.S. PATENT DOCUMENTS

| | | | |
|---|---|---|---|
| 6,200,134 B1* | 3/2001 | Kovac | A61C 19/004 362/800 |
| 7,094,054 B2 | 8/2006 | Cao | |
| 7,273,369 B2* | 9/2007 | Rosenblood | A61C 19/004 362/800 |
| 7,581,846 B2* | 9/2009 | Hayman | A61C 19/004 250/504 H |
| 8,591,078 B2* | 11/2013 | Igl | F21V 29/02 362/126 |
| 2007/0128577 A1* | 6/2007 | Scott | A61C 19/004 433/29 |
| 2007/0190479 A1* | 8/2007 | Jackson, III | A61C 19/004 433/29 |
| 2008/0096156 A1* | 4/2008 | Rose | A61C 1/0015 433/29 |
| 2009/0208894 A1* | 8/2009 | Orloff | A61C 19/004 433/29 |
| 2010/0075272 A1* | 3/2010 | Lin | A61C 19/004 433/29 |
| 2011/0236851 A1* | 9/2011 | Muller | A61C 19/004 433/29 |

(Continued)

*Primary Examiner* — Meredith Shin
(74) *Attorney, Agent, or Firm* — Muncy, Geissler, Olds & Lowe, P.C.

(57) ABSTRACT

A dental light curing device includes a first shell segment, a second shell segment coupled with the first shell segment to jointly define an installation space, and a light emitting module and a duty module located in the installation space. The first shell segment and the second shell segment have respectively a first confining rib and a second confining rib to divide the installation space into a first zone and a second zone. The light emitting module is located in the second zone to form electric connection with the duty module and be controlled to generate a curing light. The light emitting module includes a primary heat sink, a secondary heat sink located on the primary heat sink and a light emitting chip located on the secondary heat sink. The primary heat sink is hollow and includes a cooling passage and a cooling fan located in the cooling passage.

10 Claims, 7 Drawing Sheets

(56) References Cited

U.S. PATENT DOCUMENTS

| | | | | |
|---|---|---|---|---|
| 2013/0034824 A1* | 2/2013 | Wang | .................. | A61C 19/004 433/29 |
| 2013/0052607 A1* | 2/2013 | Gersh | ................. | A61C 19/004 433/27 |
| 2014/0315142 A1* | 10/2014 | Montgomery | ....... | A61C 19/066 433/29 |

* cited by examiner

DENTAL LIGHT CURING DEVICE

FIELD OF THE INVENTION

The present invention relates to a dental light curing device and particularly to a dental light curing device equipped with a light emitting module which holds a primary heat sink and a secondary heat sink and a cooling fan embedded on the primary heat sink.

BACKGROUND OF THE INVENTION

In the conventional dental surgery and therapeutic process medical people often take a suitable treatment for a patient according to the condition of the patient's decayed tooth. In the event that the decayed condition is minor, a commonly called filling treatment usually is taken to prevent the decayed tooth from deteriorating. At the present filling treatment a filling material (such as dental amalgam, resin or ceramic artificial enamel) is filled in the patient tooth, then filling material is cured to finish the treatment. In the followings the resin is used as an embodiment of the filling material to facilitate discussion. In the filling treatment patient's tooth is cleaned first; next, a suitable amount of resin is filled in the tooth; then a dental light curing device is employed to provide a curing light to cure the resin.

Nowadays the technology of light-emitting diode (LED) is well developed, hence the LED also has been adopted in the dental light curing device. For instance, U.S. Pat. No. 7,094,054 discloses such a technique. During the filling treatment a high intensity curing light has to be generated to project the filling material for curing. Hence the LED also requires a greater amount of power to generate the curing light needed. As a result, a greater amount of waste heat also is generated from the LED. The aforesaid U.S. Pat. No. 7,094,054 discloses a dental curing light which includes a primary heat sink to hold the LED, an elongated secondary heat sink connected to the primary heat sink and an air fan installed corresponding to the secondary heat sink. Through a multi-stage heat exchange process the waste heat of the LED can be dispelled. In practice, the air fan is located on the secondary heat sink remote from the primary heat sink, and can only provide cooling airflow to do heat exchange for the surface of the secondary heat sink. The cooling efficacy is not desirable. Moreover, the secondary heat sink has a lengthy heat transfer path, and the air fan can perform the heat exchange merely for a single surface of the secondary heat sink. As a result, the waste heat generated by the LED still accumulates at one end of the secondary heat sink abutting the primary heat sink. Hence it still leaves a lot to be desired in terms of usability. In addition, the elongate secondary heat sink takes a greater portion of the interior space of the dental curing light that limits arrangement of other elements. This also makes changing the size and shape of the dental curing light to meet implementation requirements more difficult.

SUMMARY OF THE INVENTION

The primary object of the present invention is to solve the problem of the conventional dental light curing device of unable to provide effective cooling for the LED.

A secondary object of the invention is to solve the problem of the conventional dental light curing device of unable to change the design of profile due to limitation caused by the cooling structure arrangement.

To achieve the foregoing objects the present invention provides a dental light curing device that includes a first shell segment, a second shell segment, a duty module and a light emitting module. The first shell segment and the second shell segment jointly define an installation space and an assembly opening communicating with the installation space. The first shell segment has a first support rib facing the second shell segment and a first confining rib spaced from the first support rib and located between the first support rib and the assembly opening. The second shell segment has a second support rib faced the first shell segment and joined the first support rib to form a support ring which divides the installation space into a first zone and a second zone that communicate with each other, and a second confining rib spaced from the second support rib and located in the second zone to join the first confining rib to form a confining ring. Moreover, at least one of the first shell segment and the second shell segment has at least one air inlet corresponding to the first zone, and also has at least one air outlet corresponding to the second zone. In addition, the duty module is located in the first zone and includes a control board, a power storage element to save electric power and supply the electric power to the control board to perform duty, and an operation element jutting from the first shell segment and the second shell segment and operable to activate the control board to perform the duty. The light emitting module is located in the second zone and forms electric connection with the duty module to receive control thereof to generate a curing light. The light emitting module includes a primary heat sink, a secondary heat sink located on the primary heat sink corresponding to the assembly opening, and at least one light emitting chip electrically laid on the secondary heat sink. The primary heat sink has a cooling dock located between the support ring and the confining ring after assembly is finished, a cooling passage run through the cooling dock, a plurality of spaced cooling pillars located on the cooling dock toward the assembly opening, a plurality of cooling vents located respectively between any two neighboring cooling pillars communicating with the cooling passage, a cooling deck connected to the cooling pillars and located in the assembly opening, a wiring trough located at one end of the cooling dock and a cooling fan located in the cooling passage and electrically connected to the duty module. The secondary heat sink includes a heat transfer plane mounted onto the cooling deck, a duty plane opposing the heat transfer plane and having an electric circuit laid thereon to hold the light emitting chip, and a power cord connected to the electric circuit and passed through the wiring trough to form electric connection with the duty module to get duty power to supply to the electric circuit. When the operation element is operated to trigger the control board, the control board controls the power storage element to supply electric power to the power cord and the cooling fan so that the light emitting chip gets the electric power and generates the curing light. The cooling fan receives the electric power and is activated to generate airflow in the installation space, and draw cooling air through the air inlet into the installation space, and pass through the cooling passage to perform heat exchange with the heat transfer plane of the cooling deck, then discharged through the cooling vents and the air outlet.

In one embodiment the cooling deck has a cross section area same as the area of the assembly opening, and smaller than that of the cooling dock.

In another embodiment the secondary heat sink has at least one first wiring hole run through the heat transfer plane and the duty plane to hold the power cord, and the wiring trough communicates with the cooling passage to hold the power cord.

In yet another embodiment the cooling deck has at least one second wiring hole corresponding to the first wiring hole to hold the power cord.

In yet another embodiment the light emitting module includes a plurality of light emitting chips that include at least one first LED chip and at least one second LED chip. The first LED chip generates the curing light of blue light at a wavelength ranged from 420 nm to 490 nm, and the second LED chip generates the curing light of ultraviolet light at a wavelength ranged from 370 nm to 410 nm.

In yet another embodiment the secondary heat sink includes an insulation layer located on the duty plane to hold the electric circuit and a protective layer covered the insulation layer and the electric circuit.

In yet another embodiment the dental light curing device further includes a mask located on the assembly opening that is hollow with an installation passage formed therein, a light guide element inserted in the installation space that has a distal end corresponding to the light emitting chip to receive and transmit the curing light, and a mask sheet located on the light guide element.

In yet another embodiment the dental light curing device further includes an ancillary shell segment corresponding to the first shell segment to couple with the second shell segment. The ancillary shell segment has a charge contact and a charge wire connected to the charge contact and the duty module.

In another embodiment the dental light curing device further includes a holding rack electrically connected to the charge contact to provide electric power to perform charging.

In yet another embodiment the first shell segment has a first notch corresponding to the first zone, and the second shell segment has a second notch corresponding to the first notch to jointly define an installation opening. The dental light curing device has an operation panel located in the installation opening to form electric connection with the control board.

The invention, through the aforesaid structure, compared with the conventional techniques, can provide the following advantages:

1. Through the cooling passage in the hollow primary heat sink and the cooling vents communicating with the cooling passage, and the cooling fan located in the cooling passage, the cooling airflow provided by the cooling fan can pass through the cooling passage to dispel heat from the cooling dock of the primary heat sink, then be discharged through the cooling vents; thus the cooling dock has a greater area to receive the cooling airflow, and can discharge the waste heat generated by the light emitting chip more effectively to resolve the problem of ineffective cooling of the conventional techniques.

2. The primary heat sink of the light emitting module is located merely in the second zone of the installation space, hence the primary heat sink can be shrunk smaller. Moreover, the cooling fan is located in the cooling passage formed in the hollow primary heat sink, hence can reduce the required installation space than the conventional structure, thereby can also resolve another problem of the convention techniques of unable to make profile change caused by limitation of the cooling structure.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
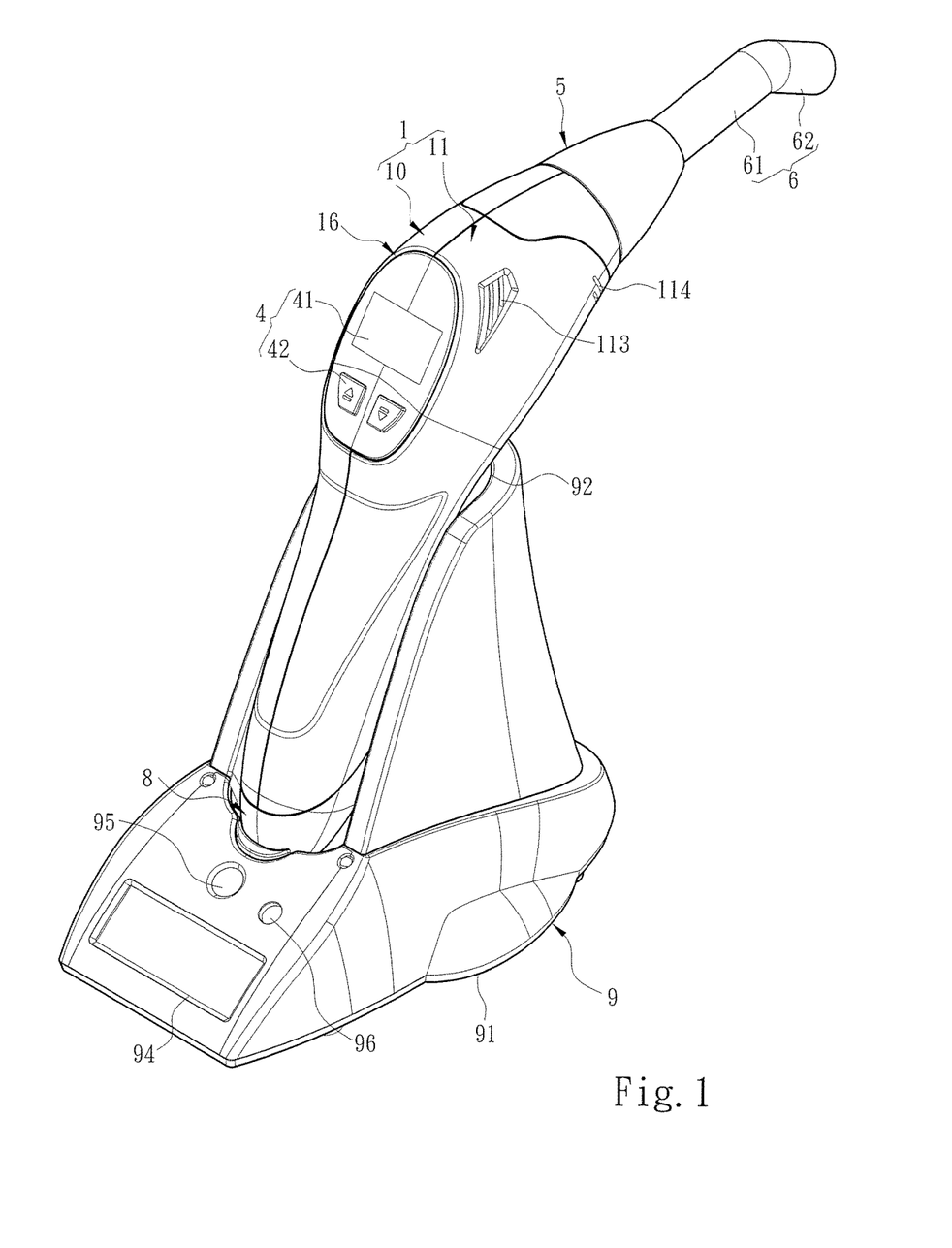
FIG. 1 is a schematic view of the structure of the dental light curing device of the invention.
Figure 2:
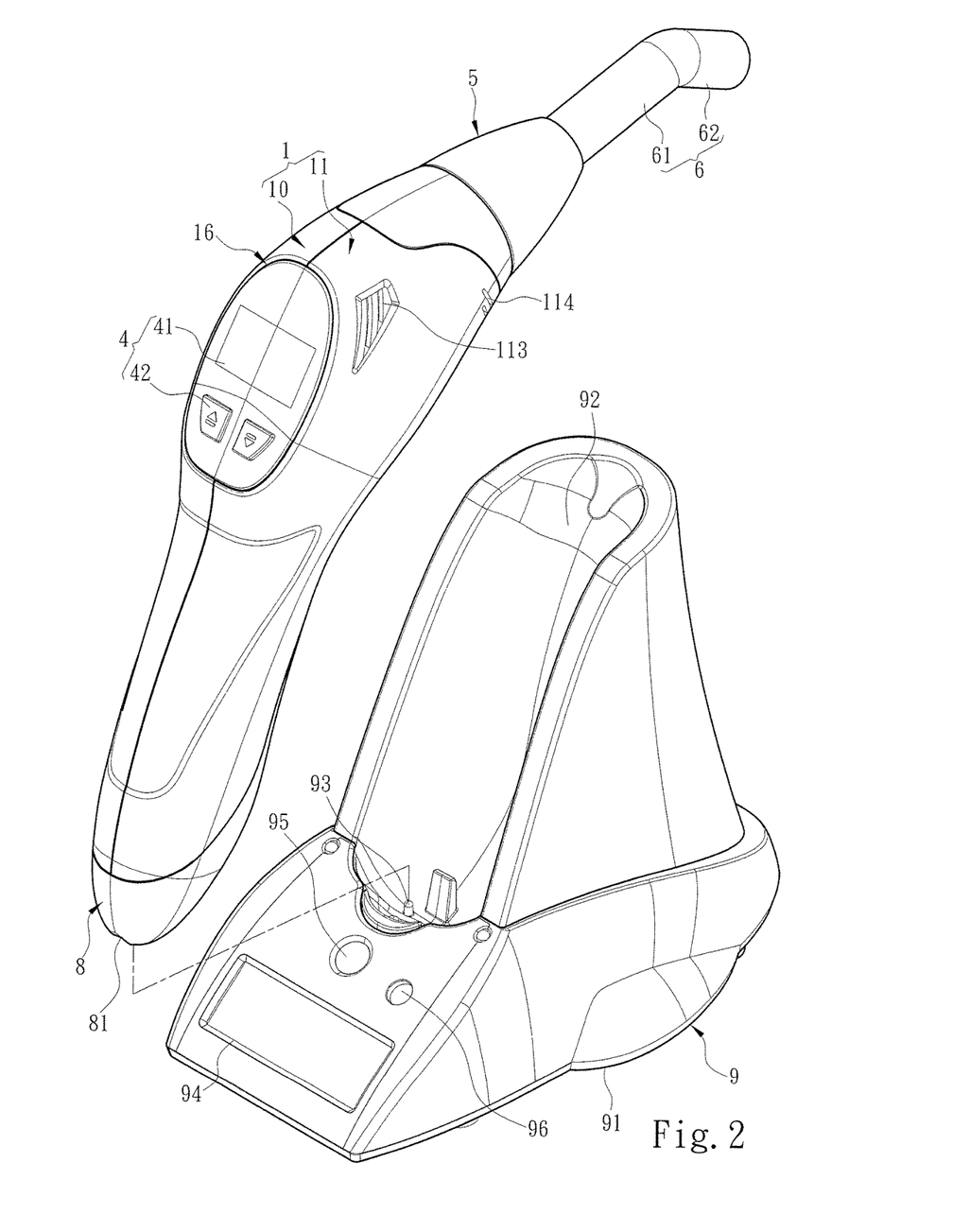
FIG. 2 is another schematic view of the structure of the dental light curing device of the invention.
Figure 3:
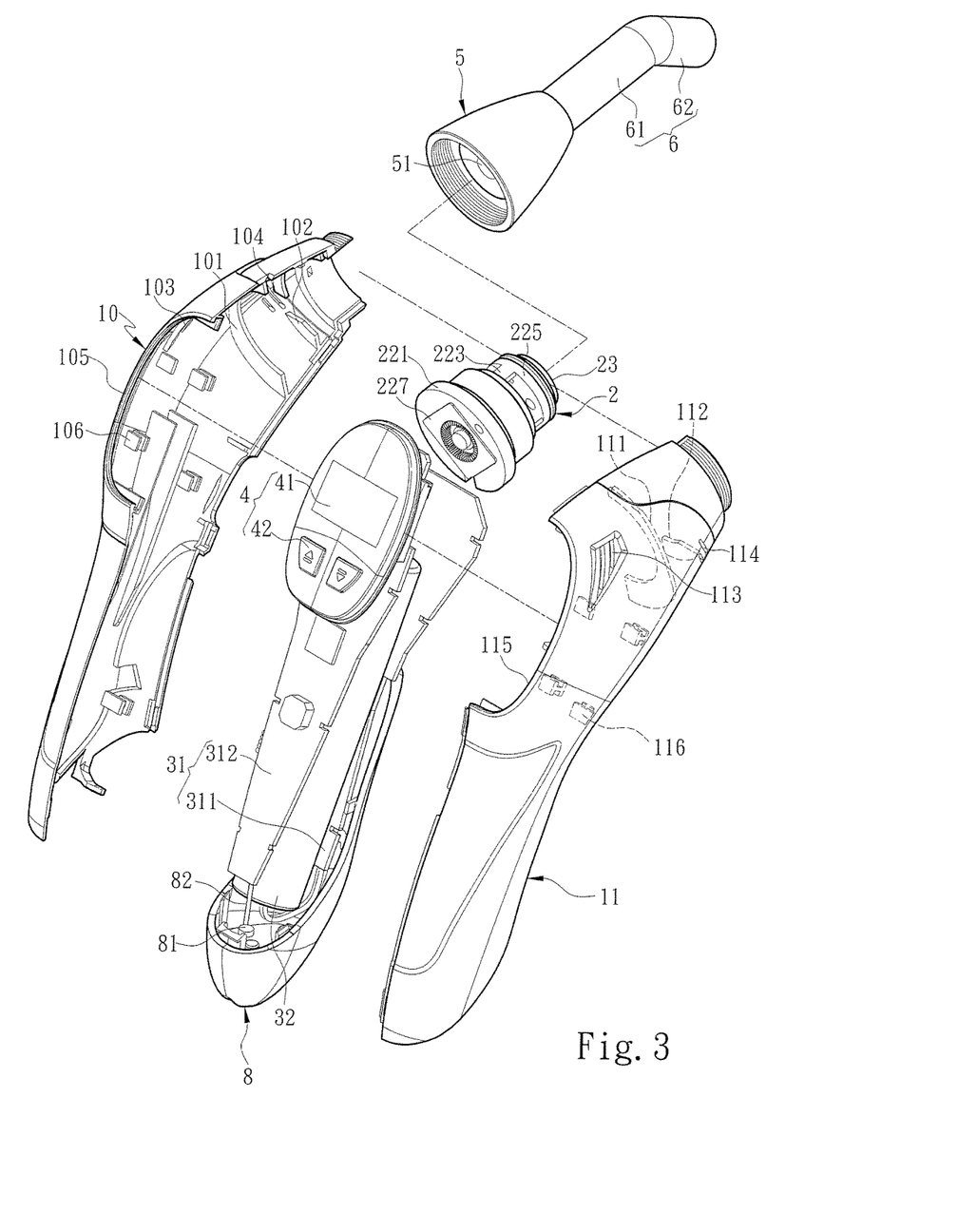
FIG. 3 is an exploded view of the structure of the dental light curing device of the invention.

Please referring to FIGS. 1 through 6, the present invention aims to provide a dental light curing device that includes a shell 1, and a light emitting module 2 and a duty module 3 located in the shell 1. The shell 1 further includes a first shell segment 10 and the second shell segment 11 that are designed and structured in a symmetrical manner, and made through a mechanical fabrication process such as injection forming such that the first shell segment 10 and the second shell segment 11 can be assembled through latching, bonding, screw fastening or the like. Furthermore, after the first shell segment 10 and the second shell segment 1 are assembled, they jointly define an installation space 12 and an assembly opening 13 communicating with the installation space 12. The first shell segment 10 has a first support rib 101 and a first confining rib 102 that are integrally formed and face the second shell segment 11. The first confining rib 102 is located between the first support rib 101 and the assembly opening 13. The second shell segment 11 has a second support rib 111 facing the first shell segment 10 and corresponding to the first support rib 101 and a second confining rib 112 corresponding to the first confining rib 102. The second support rib 111 and the second confining rib 112 also are formed integrally and spaced from each other. The second confining rib 112 is located between the second support rib 111 and the assembly opening 13, as shown in FIG. 3. After the first shell segment 10 and the second shell segment 11 are coupled together, the first support rib 101 and the second support rib 111 correspond to each other to jointly form a support ring 14, and the first confining rib 102 and the second confining rib 112 correspond to each other to jointly form a confining ring 15. The support ring 14 divides the installation space 12 into a first zone 121 and a second zone 122. More specifically, the first zone 121 is a section remote from the assembly opening 13, while the second zone is a section of the installation space 12 located between the support ring 14 and the assembly opening 13. Also referring to FIG. 6, in this invention the first zone 121 takes a greater proportion of the total assembly space 12 than the second zone 122. Moreover, in an embodiment of the invention the first shell segment 10 and the second shell segment 11 corresponding to the first zone 121 are designed in a handgrip section to be gripped by a user. The first shell segment 10 and the second shell segment 11 corresponding to the second zone 122 are designed in a duty section.

According to actual requirements after assembly of the first shell segment 10 and the second shell segment 11 is finished the shell 1 can be formed in a cane shape. In addition, referring to FIG. 6, the handgrip section and the duty section also can be formed with an included angle between them to provide improved usability for medical people. Furthermore, at least one of the first shell segment 10 and the second shell segment 11 has at least one air inlet 103 and 113 corresponding to the first zone 121, and at least one air outlet 104 and 114 corresponding to the second zone 122. Also referring to FIG. 3, in one embodiment both the first shell segment 10 and the second shell segment 11 have the air inlets 103 and 113 formed corresponding to the first zone 121, and the air outlets 104 and 114 corresponding to the second zone 122.

Figure 4:
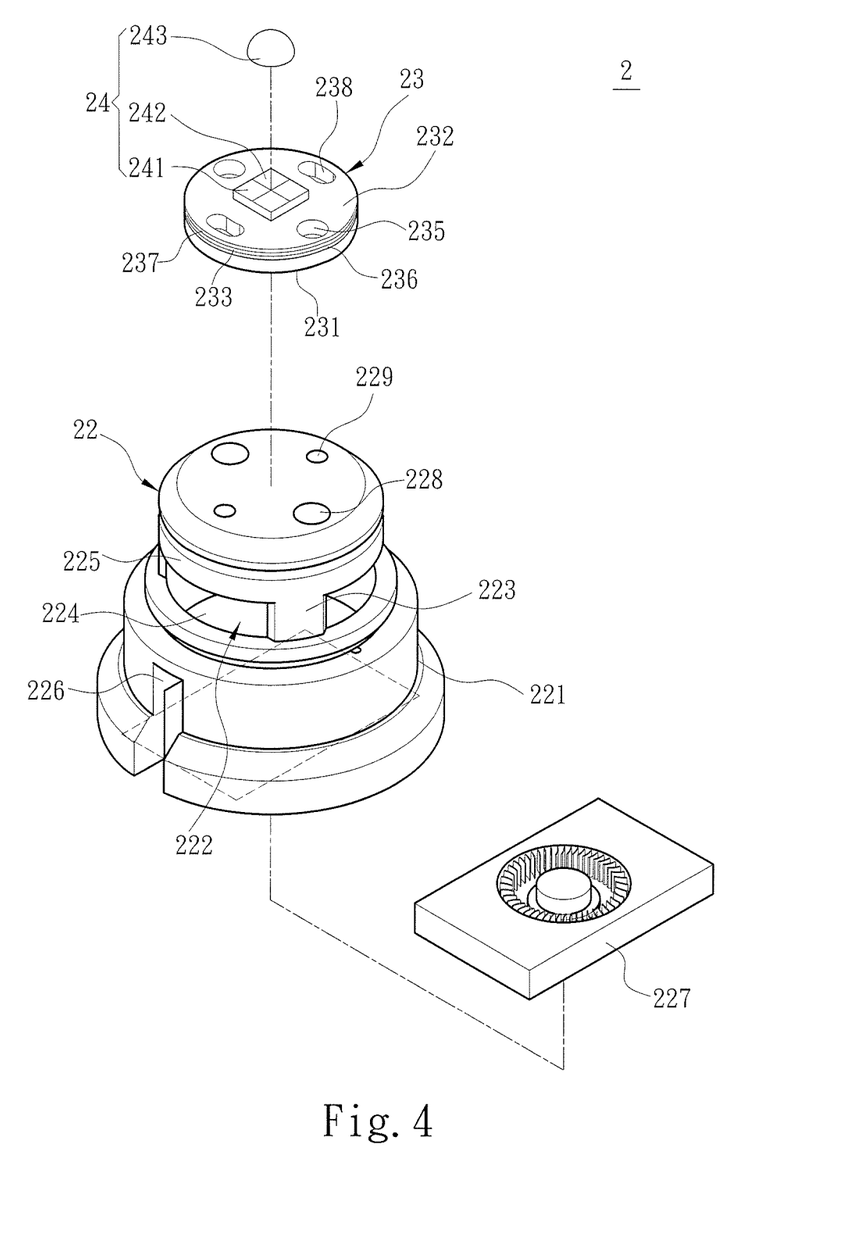
FIG. 4 is an exploded view of the light emitting module of the invention.
Figure 5:
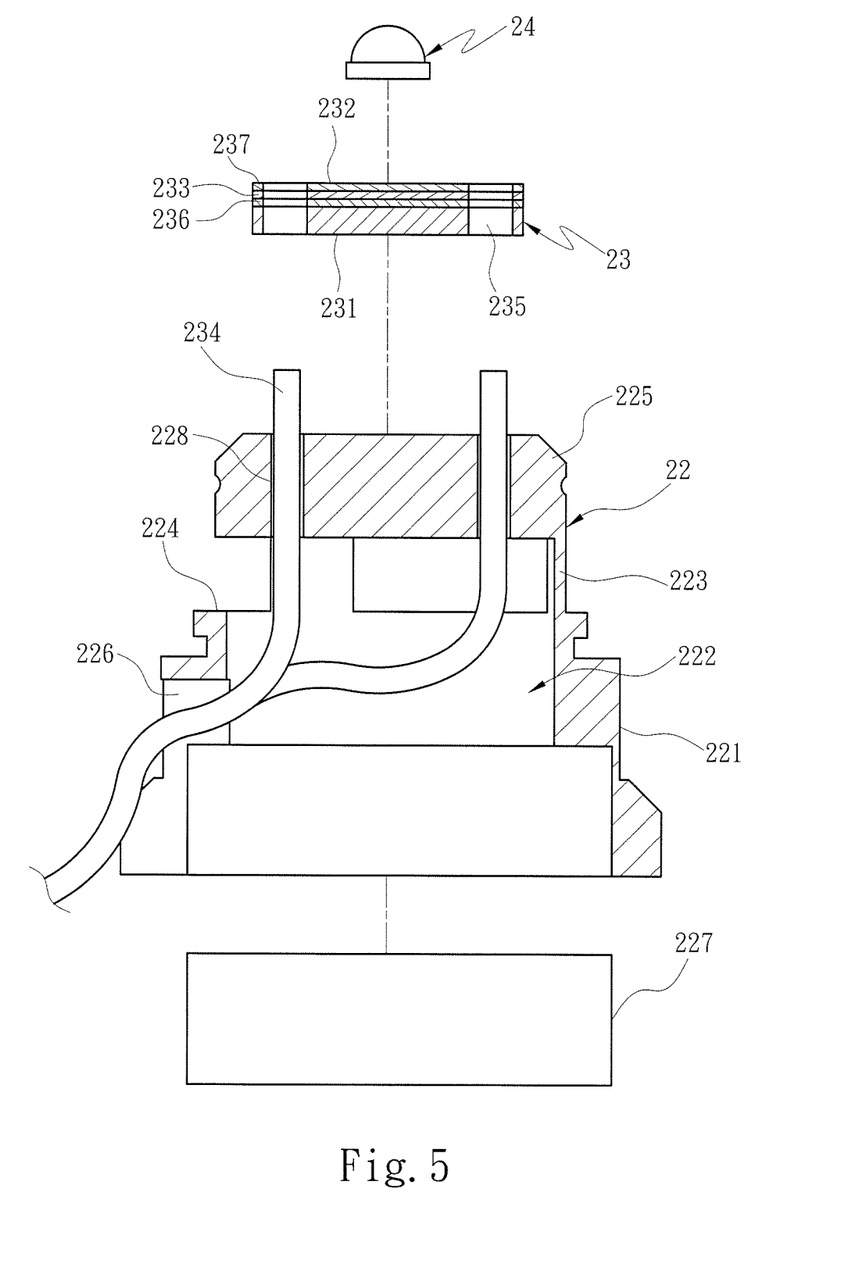
FIG. 5 is a sectional view of the light emitting module of the invention.
Figure 7:
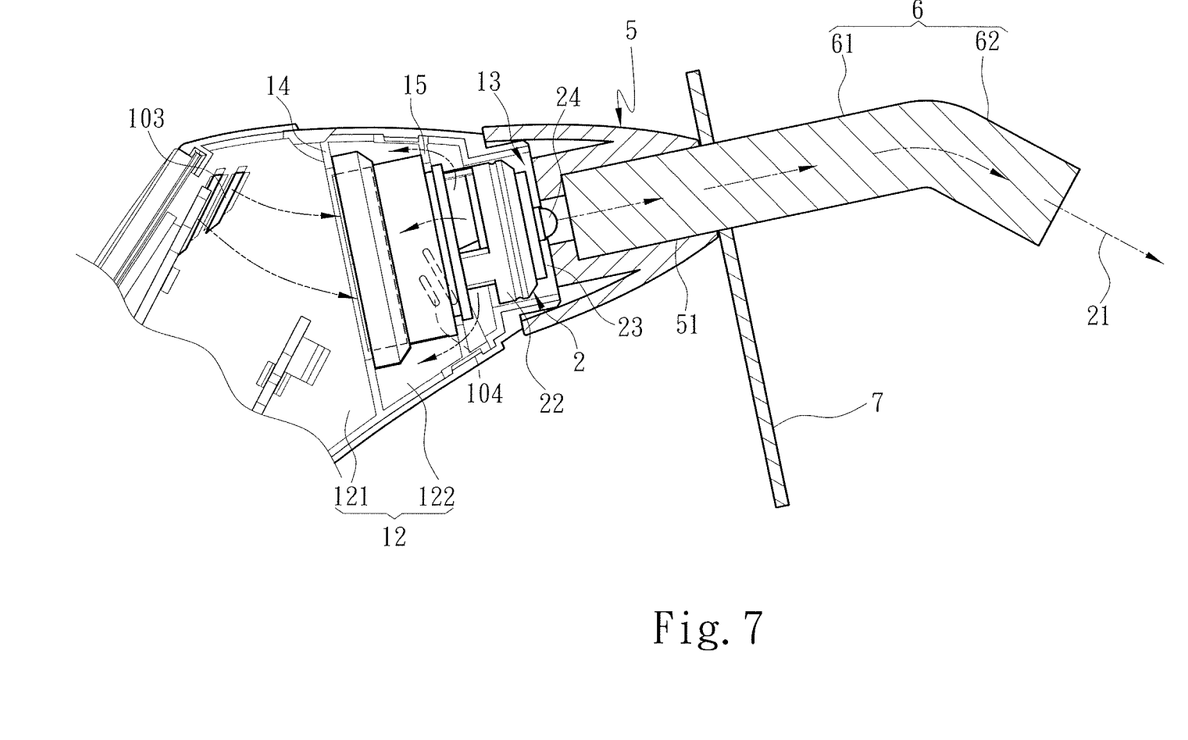
FIG. 7 is a schematic view of the dental light curing device of the invention in a use condition.

Please also referring to FIGS. 3 and 4, the light emitting module 2 is located in the second zone 122 and forms electric connection with the duty module 3 so that when the dental light curing device is in use it is controlled by the duty module 3 to generate a curing light 21 (also referring to FIG. 7). More specifically, the light emitting module 2 includes a primary heat sink 22, a secondary heat sink 23 and at least one light emitting chip 24. The primary heat sink 22 is located between the support ring 14 and the assembly opening 13 and confined by the support ring 14 and the confining ring 15. The secondary heat sink 23 is corresponding to the primary heat sink 22 and mounted thereon, and also is designed corresponding to the assembly opening 13. The light emitting chip 24 is electrically laid on the secondary heat sink 23. More specifically, the primary heat sink 22 and the secondary heat sink 23 can be made of metal, such as copper, aluminum or an alloy consisting of a plurality of metals. In another embodiment the primary heat sink 22 and the secondary heat sink 23 can be made of different materials so that through their different cooling characteristics more desirable cooling efficacy can be provided to the light emitting chip 24. Furthermore, the primary heat sink 22 includes a cooling dock 221, a cooling passage 222 run through the cooling dock 221, a plurality of spaced cooling pillars 223 located on the cooling dock 221 toward the assembly opening 13, a plurality of cooling vents 224 located respectively between any two neighboring cooling pillars 223 communicating with the cooling passage 222, and a cooling deck 225 connected to the cooling pillars 223 and located in the assembly opening 13. Furthermore, the primary heat sink 22 further includes a wiring trough 226 located at one end of the cooling dock 221 and a cooling fan 227 located in the cooling passage 222 and electrically connected to the duty module 3. The cooling fan 227 can also be positioned locally in the cooling passage 222 according to actual requirements, and can be fastened thereon by screwing or latching. In another embodiment the cooling deck 225 is formed with a cross section area same as the area of the assembly opening 13, and the cooling dock 221 is formed with a cross section area greater than that of the cooling deck 225, therefore form a narrow upper side and a wider lower side fashion so that during assembly of the primary heat sink 22 is confined by the support ring 14 and the confining ring 15 at the same time without sliding into the second zone 122.

The secondary heat sink 23 includes a heat transfer plane 231 mounted onto the cooling deck 225, a duty plane 232 opposing the heat transfer plane 231 and a power cord 234. The duty plane 232 is laid with an electric circuit 233 to hold the light emitting chip 24. The power cord 234 is connected to the electric circuit 233 to form electric connection with the duty module 3 through the wiring trough 226 of the primary heat sink 22 to get duty power to supply the electric circuit 233. Furthermore, the secondary heat sink 23 has at least one first wiring hole 235 run through the heat transfer plane 231 and the duty plane 232 to hold the power cord 234. The cooling deck 225 has at least one second wiring hole 228 corresponding to the first wiring hole 235 to hold the power cord 234. Thus, the power cord 234 can pass through the first wiring hole 235 and the second wiring hole 228 to enter the cooling vents 224, then pass through the wiring trough 226 of the primary heat sink 22 to connect to the duty module 3 so that the electric power of the duty module 3 can be transmitted to the light emitting chip 24 to generate light. In addition, depending on requirements, the secondary heat sink 23 can further include at least one first fastening hole 238, and the primary heat sink 22 can have at least one second fastening hole 229 corresponding to the first fastening hole 238 so that they can be fastened together via a fastener. Also referring to FIG. 5, the secondary heat sink 22 can be made of metal to ensure that the light emitting chip 24 can function normally. The secondary heat sink 23 also has an insulation layer 236 located on the duty plane 232 to hold the electric circuit 233 and a protective layer 237 to cover the insulation layer 236 and the electric circuit 233.

The light emitting module 2 has a plurality of light emitting chips 24 located thereon. In one embodiment, referring to FIG. 4, four light emitting chips 24 are provided as an example for discussion, but this is not the limitation of the invention. Furthermore, the light emitting chips 24 include a first LED chip 241 and a second LED chip 242. The first LED chip 241 generates the curing light 21 of blue light at a wavelength ranged from 420 nm to 490 nm, while the second LED chip 242 generates the curing light 21 of ultraviolet light at a wavelength ranged from 370 nm to 410 nm. Thus the light emitting module 2 can provide the curing light 21 included the blue light and the ultraviolet light at the same time. Moreover, the light emitting chips 24 are covered by a protective sealing resin 243.

Figure 6:
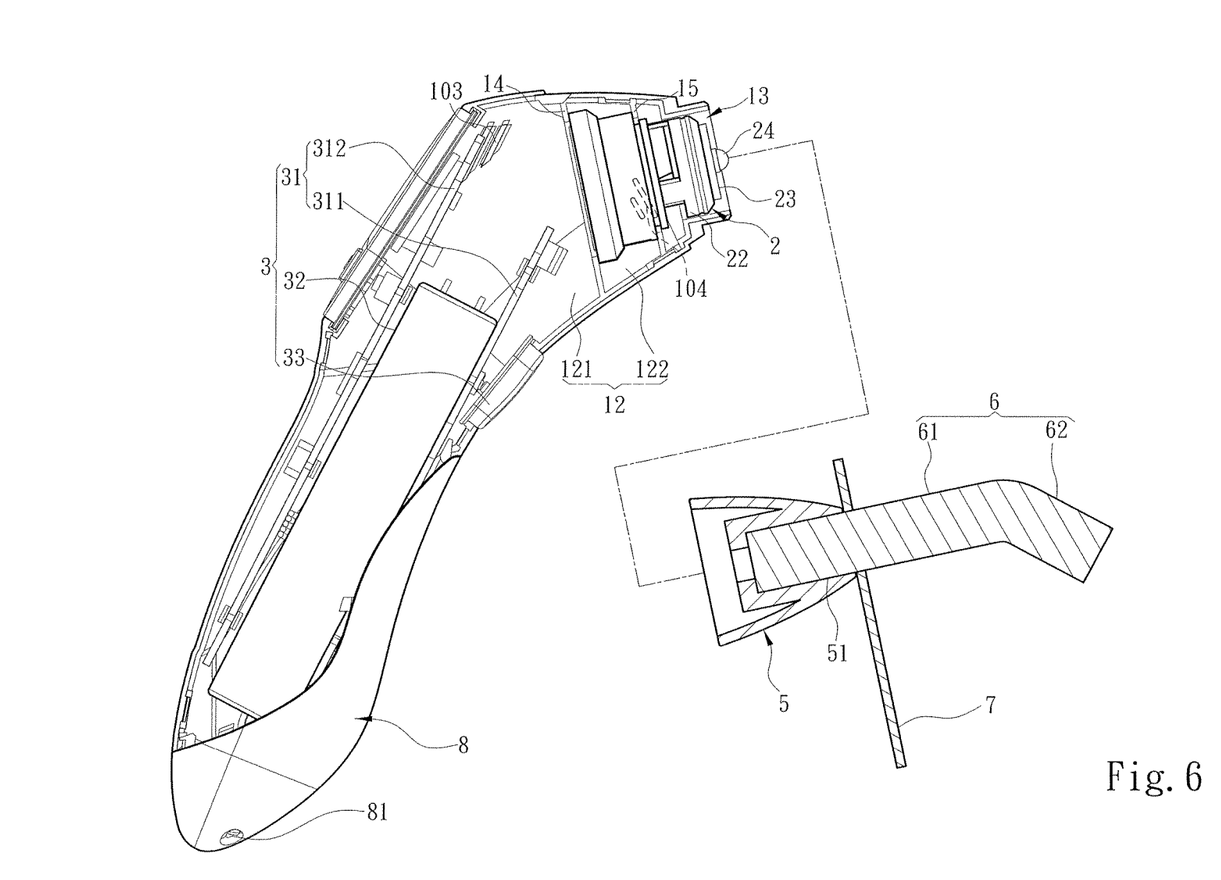
FIG. 6 is a sectional view of the dental light curing device of the invention.

Please referring to FIGS. 3 and 6, the duty module 3 is located in the first zone 121 and includes a control board 31, a power storage element 32 and an operation element 33. The control board 31 is laid with at least one control circuit which is operable to control the light emitting module 2 to perform duty as desired. The power storage element 32 saves electric power for operation of the control board 31 and the light emitting module 2. The operation element 33 is a button, and can be designed jutting from the first shell segment 10 and the second shell segment 11. Namely, the operation element 33 is protrudent from the shell 1 to be used by users in operation. In one embodiment the first shell segment 10 has a notch at the first zone 121, and the second shell segment 11 has another notch at a corresponding location to jointly form a final notch after the first shell segment 10 and the second shell segment 11 are coupled together to hold the operation element 33 to be jutting from the shell 1. In another embodiment the control board 31 includes a main duty board 311 and a sub-duty board 312 that have respectively a portion of the control circuit laid thereon and form electric connection between them so that electric signals are transmittable between the main duty board 311 and the sub-duty board 312. In addition, in this embodiment the power storage element 32 is located between the main duty board 311 and the sub-duty board 312. The first shell segment 10 and the second shell segment 11 can further have respectively an installation rib 106 and 116 formed thereon for assembly of the main duty board 311 and the sub-duty board 312. The duty module 3 further includes an operation panel 4 which is electrically connected to the control board 31 to get display information from the control board 31 and display thereof. In this embodiment the first shell segment 10 has a first notch 105, and the second shell segment 11 has a second notch 115 corresponding to the first notch 105 to jointly form an installation opening 16 to hold the operation panel 4 after the first shell segment 10 and the second shell segment 11 are coupled together. Moreover, the operation panel 4 has a display panel 41 and at least one operation button 42. Hence the user can provide a control signal to the control panel 31 through the operation button 42 to order the control panel 31 to perform a corresponding task. The display panel 41 allows medical people to understand onsite operation conditions. In yet another embodiment the dental light curing device can provide three types of light emission mode, that are a full power mode, a ramp-up mode and a pulse mode. In the full power mode the control board 31 provides rated duty power to the light emitting module 2 to generate the curing light at full intensity. In the ramp-up mode the control board 31 increases gradually output power to the light emitting module 2 according to a duty timeline so that the intensity of the curing light changes gradually from dim to brighter. In the pulse mode the control board 31 supplies the power to the light emitting module 2 in an intermittent manner so that the light emitting module 2 can generate pulsed light. In addition, in yet another embodiment the medical people can select the light emission mode of the light emitting chips 24 through the operation button 42, and determine whether the curing light 21 is generated individually by the first LED chip 241 or the second LED chip 242, or by both the first LED chip 241 and the second LED chip 242 at the same time. Please also referring to FIGS. 1, 2 and 3, in yet another embodiment the dental light curing device further includes a mask 5 on the assembly opening 13 that is hollow with an installation passage 51 formed therein, a light guide element 6 connected to the installation passage 51, and a mask sheet 7 located on the light guide element 6. The connected light guide element 6 has one end corresponding to the light emitting module 3 to receive and transmit the curing light 21. Furthermore, the light guide element 6 includes a light guide section 61 corresponding to the light emitting module 3 and a light exit section 62 extended integrally from the light guide section 61. The light guide element 6 can be selectively detached from the mask 5 for high temperature sterilization after use. Moreover, the mask sheet 7 is located on the light guide element 6 to alleviate discomfort of the eyes of the medical people caused by reflection of the curing light 21.

Please referring to FIGS. 1, 2 and 3 again, in yet another embodiment the dental light curing device further includes an ancillary shell segment 8 corresponding to assembly of the first shell segment 10 and the second shell segment 11. The ancillary shell segment 8 includes a charge contact 81 and a charge wire 82 to bridge the charge contact 81 and the duty module 3. Furthermore, in this embodiment, the dental light curing device further includes a holding rack 9 which includes a base 91, a loading portion 92 extended from the base 91 to hold the shell 1, a power supply contact 93 located on the loading portion 92 to form conduction with the charge contact 81, a display 94 located on the base 91, a light sensor 95 located on the base 91 and a detection switch 96 electrically connected to the light sensor 95. During operation the base 91 has a charge module (not shown in the drawings) connectable to an external power source and electrically connected to the power supply contact 93 so that when the shell 1 is held on the loading portion 92 the charge module gets electric power from the external power source that is transmitted via the power supply contact 93 to the charge contact 81 to charge the power storage element 32. In addition, after the dental light curing device has been repeatedly used, the light emitting chips 24 could attenuate. To address this issue, the medical people can project the curing light 21 to the light sensor 95 to generate a test value output to the display 94. The light sensor 95 can test characteristics of the curing light 21, such as light intensity, light temperature and the like. Through the detection switch 96 the medical people can change the test characteristics performed by the light sensor 95 and display the test results on the display 94.

Please referring to FIG. 7, when the dental light curing device of the invention is in use the operation element 33 is maneuvered to trigger the control board 31 to function; the control board 31 controls the power storage element 32 to supply electric power to the power cord 234 and the cooling fan 227 so that the light emitting chips 24 get the electric power to generate the curing light 21, and the cooling fan 227 is activated and spins to generate airflow in the installation space 12, and cooling air is drawn through the air inlets 103 and 113 into the installation space 12, and passes through the cooling passage 222 to perform heat exchange with the heat transfer plane 231 on the cooling deck 225, then is discharged through the cooling vents 224 and the air outlets 104 and 114. Moreover, while the light emitting chips 24 generate the curing light 21 the waste heat being generated also is transferred from the duty plane 232 of the secondary heat sink 23 to the heat transfer plane 231; as the duty plane 232 is located on the cooling dock 221 of the primary heat sink 22, the waste heat can be transferred via thermal conduction to the heat transfer plane 231 and the cooling deck 225 of the primary heat sink 22. Due to the cooling dock 221 is made holistically of the same metal, the waste heat can be transferred from the cooling deck 225 to the cooling pillars 223 and the cooling dock 221. While the light emitting module 2 is in operation the cooling fan 227 generates airflow in the installation space 12 to form cooling airflow which is directed by the cooling fan 227 to enter the first zone 121 of the installation space 12 via the air inlets 103 and 113, and passes through the cooling fan 227 and the cooling passage 222 to be in contact with the cooling deck 225, so that the cooling airflow generates heat exchange with the cooling dock 221, the cooling pillars 223 and the cooling deck 225 at the same time, and dispels the waste heat accumulated on the cooling dock 221; finally, the cooling airflow passes through the cooling vents 224 again and enters the second zone 122, and is discharged via the air outlets 104 and 114.

As a conclusion, the dental light curing device of the invention includes a first shell segment, a second shell segment joined the first shell segment to define an installation space, a light emitting module and a duty module located in the installation space. The first shell segment and the second shell segment have respectively a first confining rib and a second confining rib to divide the installation space into a first zone and a second zone. The light emitting module is located in the second zone and electrically connected to the duty module and controllable to generate a curing light. The light emitting module includes a primary heat sink, a secondary heat sink located on the primary heat sink and a light emitting chip located on the secondary heat sink. The primary heat sink is hollow with a cooling passage inside and a cooling fan located in the cooling passage. Thus, the invention can provide improvement for the ineffective cooling problem of the light emitting module occurred to the conventional techniques, and also resolve the structural design limitation problem of the conventional dental light curing devices.

What is claimed is:

1. A dental light curing device, comprising:
   a first shell segment and a second shell segment that jointly define an installation space and an assembly opening communicating with the installation space, the first shell segment including a first support rib facing the second shell segment and a first confining rib spaced from the first support rib and located between the first support rib and the assembly opening, the second shell segment including a second support rib facing the first shell segment to join the first support rib to form a support ring which divides the installation space into a first zone and a second zone that communicate with each other, and a second confining rib spaced from the second support rib and located in the second zone to join the first confining rib to form a confining ring, at least one of the first shell segment and the second shell segment including at least one air inlet corresponding to the first zone and at least one air outlet corresponding to the second zone;
   a duty module which is located in the first zone and includes a control board, a power storage element to save electric power and supply the electric power to the control board for operation thereof, and an operation element jutting from the first shell segment and the second shell segment that is operable to activate the control board to perform duty; and
   a light emitting module which is located in the second zone and electrically connected to the duty module to be controlled thereof to generate a curing light and includes a primary heat sink, a secondary heat sink located on the primary heat sink corresponding to the assembly opening and at least one light emitting chip electrically laid on the secondary heat sink, the primary heat sink including a cooling dock located between the support ring and the confining ring, a cooling passage running through the cooling dock, a plurality of cooling pillars located in a spaced manner on the cooling dock toward the assembly opening, a plurality of cooling vents located respectively between any two neighboring cooling pillars to communicate with the cooling passage, a cooling deck connected to each of the cooling pillars and located in the assembly opening of the cooling passage, a wiring trough located at one end of the cooling dock and a cooling fan located on the cooling dock in the cooling passage and electrically connected to the duty module; the secondary heat sink including a heat transfer plane mounted onto the cooling deck and in surface contact with the cooling deck, a duty plane opposing the heat transfer plane and having an electric circuit laid thereon to hold the light emitting chip, and the secondary heat sink including a power cord electrically connected to the duty module and passed through the wiring trough to form electric connection with the duty module to get duty power to supply the electric circuit;
   wherein the operation element is operable to trigger the control board to control the power storage element to supply electric power to the power cord and the cooling fan such that the light emitting chip gets the electric power and operates to generate the curing light, the cooling fan receiving the electric power and being activated to generate airflow in the installation space and draw cooling airflow through the air inlet into the installation space and to pass through the cooling passage to perform heat exchange with the heat transfer plane on the cooling deck, and to be discharged through the cooling vents and the air outlet.

2. The dental light curing device of claim 1, wherein the cooling deck has a cross section area as same as an area of the assembly opening, and the cooling dock has a cross section area greater than that of the cooling deck.

3. The dental light curing device of claim 1, wherein the secondary heat sink includes at least one first wiring hole running through the heat transfer plane and the duty plane to hold the power cord, the wiring trough communicating with the cooling passage to hold the power cord.

4. The dental light curing device of claim 3, wherein the cooling deck includes at least one second wiring hole corresponding to the first wiring hole to hold the power cord.

5. The dental light curing device of claim 1, wherein the light emitting module includes a plurality of light emitting chips that include at least one first LED chip and at least one second LED chip, the first LED chip generating the curing light of blue light at a wavelength ranged from 420 nm to 490 nm, the second LED chip generating the curing light of ultraviolet light at a wavelength ranged from 370 nm to 410 nm.

6. The dental light curing device of claim 1, wherein the secondary heat sink includes an insulation layer located on the duty plane to hold the electric circuit and a protective layer to cover the insulation layer and the electric circuit.

7. The dental light curing device of claim 1 further including a hollow mask located on the assembly opening, a light guide element connected to the installation space and included a distal end corresponding to the light emitting chip to receive and transmit the curing light, and a mask sheet located on the light guide element.

8. The dental light curing device of claim 1 further including an ancillary shell segment which is corresponding to the first shell segment and coupled with the second shell segment, and includes a charge contact and a charge wire connected to the charge contact and the duty module.

9. The dental light curing device of claim 8 further including a holding rack to form electric connection with the charge contact to provide electric power to perform charging.

10. The dental light curing device of claim 1, wherein the first shell segment includes a first notch corresponding to the first zone, the second shell segment including a second notch corresponding to the first notch to jointly define an installation opening, the dental light curing device including an operation panel located in the installation opening and formed electric connection with the control board,
   wherein the operation panel and the operation element are located at two sides of the dental light curing device.

* * * * *